United States Patent
Wiechmann et al.

(10) Patent No.: US 9,517,126 B2
(45) Date of Patent: Dec. 13, 2016

(54) OPHTHALMOLOGIC IMPLANT

(75) Inventors: Martin Wiechmann, Jena (DE); Mario Gerlach, Hohen Neuendorf (DE)

(73) Assignee: Carl Zeiss Meditec AG, Jena (DE)

( * ) Notice: Subject to any disclaimer, the term of this patent is extended or adjusted under 35 U.S.C. 154(b) by 282 days.

(21) Appl. No.: 12/935,861

(22) PCT Filed: Mar. 24, 2009

(86) PCT No.: PCT/EP2009/053453
§ 371 (c)(1),
(2), (4) Date: Jul. 8, 2011

(87) PCT Pub. No.: WO2009/124838
PCT Pub. Date: Oct. 15, 2009

(65) Prior Publication Data
US 2011/0264209 A1    Oct. 27, 2011

(30) Foreign Application Priority Data
Apr. 7, 2008  (DE) .......... 10 2008 017 592

(51) Int. Cl.
*A61F 2/14* (2006.01)
*A61F 2/16* (2006.01)
(Continued)

(52) U.S. Cl.
CPC . *A61F 2/14* (2013.01); *A61F 2/16* (2013.01); *A61F 2/1613* (2013.01); *A61F 9/00* (2013.01);
(Continued)

(58) Field of Classification Search
CPC ......... A61F 2/1613; A61F 2/16; A61F 2/1616
(Continued)

(56) References Cited

U.S. PATENT DOCUMENTS 4,490,860 A    1/1985  Rainin
4,528,311 A *  7/1985  Beard et al. ................. 524/91
(Continued)

FOREIGN PATENT DOCUMENTS

EP    0 402 825 A1    12/1990
EP    1 225 441 A2 *   7/2002 ............. G01N 21/64
(Continued)

OTHER PUBLICATIONS

International Patent Application No. PCT/EP2009/053453, English Translation of International Preliminary Report on Patentability Chapter II (IPEA/409), dated Jan. 13, 2011, 5 pages (corresponds to U.S. Appl. No. 12/935,861).

(Continued)

*Primary Examiner* — Thomas J Sweet
*Assistant Examiner* — Leslie Lopez
(74) *Attorney, Agent, or Firm* — Fitch, Even, Tabin & Flannery LLP (57) ABSTRACT

The invention relates to an ophthalmologic implant, in particular an intraocular lens. The implant includes at least one marker produced with at least one dye which is a fluorescent dye having a maximum emission outside of the light spectrum visible to humans or an absorbing dye having a maximum absorption outside the light spectrum visible to humans. The said fluorescent or absorbing dye does not substantially influence light transmission of the ophthalmologic implant within the visual spectral range. The invention further relates to a microscopy system and an optical detection process for detecting and/or identifying the disclosed ophthalmologic implant.

17 Claims, 5 Drawing Sheets

(51) Int. Cl.
*A61F 9/00* (2006.01)
*A61L 27/50* (2006.01)

(52) U.S. Cl.
CPC ........ *A61L 27/50* (2013.01); *A61F 2250/0098* (2013.01); *A61L 2430/16* (2013.01)

(58) Field of Classification Search
USPC ........................................ 623/6.17, 6.56, 6.6
See application file for complete search history.

(56) References Cited

U.S. PATENT DOCUMENTS

| | | | |
|---|---|---|---|
| 4,632,773 | A | 12/1986 | Neefe |
| 4,743,255 | A | 5/1988 | Bardenstein |
| 6,634,747 | B1 * | 10/2003 | Atkins et al. ............ 351/159.69 |
| 7,053,997 | B2 | 5/2006 | Suzuki et al. |
| 2002/0146161 | A1 * | 10/2002 | Suzuki et al. ................ 382/141 |
| 2004/0032566 | A1 | 2/2004 | Nakada et al. |
| 2005/0206843 | A1 * | 9/2005 | Nakada et al. ................ 351/159 |
| 2006/0050146 | A1 | 3/2006 | Richardson |
| 2006/0199105 | A1 * | 9/2006 | Cahill ...................... 430/270.11 |
| 2006/0235428 | A1 | 10/2006 | Silvestrini |
| 2006/0265058 | A1 * | 11/2006 | Silvestrini ................... 623/5.13 |
| 2007/0171363 | A1 | 7/2007 | Chen et al. |

FOREIGN PATENT DOCUMENTS

| | | |
|---|---|---|
| GB | 2 100 878 A | 1/1983 |
| JP | 2005204723 A | 8/2005 |
| WO | 2005050192 A1 | 6/2005 |
| WO | 2007/120755 A2 | 10/2007 |

OTHER PUBLICATIONS

Von Deffer H. et al., "Infrared Diagnosis in Ophthalmology," vol. 96, No. 20, May 25, 1978, pp. 1053-1057, Germany.

* cited by examiner

OPHTHALMOLOGIC IMPLANT

CROSS REFERENCE TO RELATED APPLICATIONS

This application is a national phase application of International Application No. PCT/EP2009/053453, filed Mar. 24, 2009, designating the United States and claiming priority to German Patent Application No. 10 2008 017 592.7, filed Apr. 7, 2008, both of which are incorporated by reference herein in their entirety.

TECHNICAL FIELD

The invention relates to an ophthalmologic implant, in particular an intraocular lens, including at least one mark produced with at least one dye.

PRIOR ART

In the implantation of ophthalmologic implants, in particular upon inserting intraocular lenses into the human eye, special illumination conditions are required to be able to represent the implant in recognizable manner. This is due to the fact that intraocular lenses usually constitute highly transparent optical elements and intraocular lenses and those regions of the eye, into which the intraocular lens is to be inserted, usually have nearly the same refractive index. In order to be able to determine the posture and position of such ophthalmologic implants to some degree, by suitable illumination techniques, a sufficiently great contrast between the implant and the regions of the eye surrounding the implant is achieved in the surgical field. For this, for example in cataract surgeries, the so-called "red reflex" is used. Therein, lens residues of a patient's eye can for example be presented and seen with a microscope with high contrast. However, it is disadvantageous in such illuminations that they can only be relatively expensively realized. A further possibility for representing the posture and position of an intraocular lens within a patient's eye is described in US 2004/0068317 A1. Therein, an intraocular lens is disclosed, the edge attaching means of which, the so-called haptics, are colored with permanently visible marks. From EP 0 402 825 A1, a further intraocular lens with marks is known, wherein the marks are made of fluorescent dyes and the dyes fluoresce within the light spectrum visible to the human. However, the known intraocular lenses with marks are disadvantageous in that with permanently visible marks, the effective pupil aperture of the patient and in particular the light transmission of the implant in the visual spectral range are considerably restricted on the one hand. In addition, transmission modulations near the pupil of the eye can result in undesired photic phenomena by diffraction effects (phase disturbance e.g. at the edges). On the other hand, even with use of dyes fluorescing in the light spectrum visible to the human, there arises the disadvantage that for example upon solar irradiation, these dyes are excited and correspondingly fluoresce. Thereby, considerable impairment of the visual sensation of view of the implant or lens wearer arises since great influence of the light transmission of the implant or of the intraocular lens in the visual spectral range is caused by the fluorescence. In addition, superposition of the ambient light is caused by the additional diffuse light (fluorescent light), thereby deteriorating the visual sensation of view due to a considerably reduced contrast.

From US 2006/235428 A1, an ocular implant is known, which has marks. There is also disclosed only very generally that this mark can be a dye, which absorbs ultraviolet light and fluoresces in the visible spectral range and thus emits light in the visible spectral range.

In VON DEFFER H; MERTZ M; WARTH P; KÖHLER H W: "Infrared diagnosis in ophthalmology" FORTSCHRITTE DER MEDIZIN, vol. 96, No. 20, May 25, 1978 (1978 May 25), pages 1053-1057, XP009121167 Germany, West, the detection of pigment distributions in the iris of the human eye is only generally discussed.

PRESENTATION OF THE INVENTION

It is the object of the present invention to provide an ophthalmologic implant of the initially mentioned type, the posture and position of which can be surely detected and/or the identification of which is possible without impairment of the visual sensation of view of an implant wearer.

This object is solved by an ophthalmologic implant according to claim 1. Advantageous developments of the invention are specified in the respective dependent claims.

An ophthalmologic implant according to the invention, in particular an intraocular lens, includes at least one mark, which is made with at least one dye, wherein the dye is a fluorescent dye with an emission maximum outside of the light spectrum visible to the human, or an absorbing dye with an absorption maximum outside of the light spectrum visible to the human, each without substantially influencing the light transmission of the implant in the visual spectral range, which is between ca. 380 nm and 780 nm or a partial range of the visual spectral range between ca. 450 nm and 750 nm. Thereby, it is possible to dispose permanent marks on the ophthalmologic implant, which do not influence the light transmission of the implant in the visual spectral range on the one hand, and fluoresce or absorb outside of the light spectrum visible to the human on the other hand, such that reliable and secure detection of the posture and position and/or identification of the implant based on the mark without influencing or impairing the visual sensation of view of the implant wearer is allowed with corresponding illumination of the implant. In addition, determination of a front and back side of the implant by means of suitable marks, such as for example asymmetric shapes and figures, letters, digits or texts, is possible without doubt. Furthermore, it is advantageously possible to irradiate the implant or the included mark in case of a suitable dye with white light or with light of a suitable spectral range, and hereby to effect corresponding fluorescence or absorption of the dye or the mark outside of the light spectrum visible to the human. Expensive illumination means are not required. However, it is also possible that excitation light with a predetermined wavelength range is used for the dye of the mark.

The fluorescent dye is selected from one of the structural classes including cyanines, merocyanines, phthalocyanines, rhodamines, porphyrines, chlorophylls, triarylmethanes, xanthenes, oxazines, thiazines, safranines, heterocyclic pyrylium and thiapyrylium salts, perrylenes, terrylenes, quaterrylenes, quaterneles, azo dyes, metal complexes or chinones. However, it is also possible that the light absorbing dye is an UV absorber of one of the structural classes including benzophenones, benzotriazoles, salicylic acid esters, resorcinmonobenzoates, oxalic acid anilides, cinnamic acid ester derivatives, p-hydroxy benzoic acid esters, and/or an IR absorber of one of these structural classes. Other florescent or absorbing dyes are also usable for producing the marks. However, it is crucial therein that the dye fluoresces or absorbs outside of the light spectrum visible to the human. Furthermore, the dye must not result in a visible opacity or stain of the ophthalmologic implant significantly influencing the sensation of view of the implant wearer or resulting in considerably worse light transmission. Advantageously, the dye is additionally biocompatible and stabile with respect to the environmental conditions in the human eye, defined by the surrounding medium, the temperature and the light effect in the UV/VIS/IR range. In addition, the dye has to be resistant to washout by for example the aqueous humor of the eye. The dye mark can also be sealed or shielded from the region surrounding the implant for example by means of a transparent foil or a coating. In using hydrophobic and hydrophilic acrylate materials for producing the ophthalmologic implant, the dye has to be able to be incorporated into or adhered to these materials. Therein, the previously described dye criteria in particular have to be satisfied by the dyes or marks in the state bound to the implant. Suitable dyes fluorescing in the infrared spectral range have for example a fluorescence wavelength between 820 nm and 1100 nm. Therein, the excitation wavelengths are between 750 nm and 850 nm. As exemplary for such a fluorescent dye, indocyanine green is to be mentioned, the excitation wavelength of which is between 700 nm and 800 nm and the fluorescence wavelengths of which are between 805 nm and 950 nm with an emission maximum at 835 nm. Further suitable dyes fluorescing in the infrared range, are known under the substance names NIR1, NIR820, SNIR2 and SNIR4.

Since ophthalmologic implants are made of hydrophobic or hydrophilic acrylate materials in many fields of application, the dyes usable for the implant according to the invention can be incorporated into or adhered to these acrylate materials. In particular, the material polymethyl methacrylate (PMMA) has proven suitable for ophthalmologic implants, in particular intraocular lenses. However, the implant can also be composed of soft hydrophilic copolymers consisting of at least one hydrophilic monomer (e.g. HEMA) and at least one hydrophobic monomer, e.g. an alkoxyalkyl methacrylate monomer such as EOEMA or MMA. Combinations with other (meth)acrylate monomers as well as combinations of HEMA+collagen compounds are also conceivable.

However, the implant can also be composed of soft hydrophobic copolymers consisting of at least two hydrophobic monomer components with different glass transition temperature, e.g. phenylacrylate+phenylmethacrylate.

In addition, silicon can be used as implant material.

By the ophthalmologic implants according to the invention, it is possible to securely and reliably represent and determine the posture and position for example of an intraocular lens during or after a surgical procedure by means of a suitable microscopic system. Furthermore, a reliable identification method for identifying the implant results, because manufacture-specific data of the implant, such as for example optical data or the date of manufacture, can also be displayed and determined besides posture and position data.

In further advantageous developments of the implant according to the invention, the at least one mark is formed on at least one attachment element and/or a lens body and/or and edge of the lens body of the ophthalmologic implant. Therein, the mark can be formed as a geometric shape, in particular as a dot, dash, cross, circle, semicircle, oval, square, rectangle, polygon or a combination of the geometric shapes. Other geometric shapes are also conceivable. Furthermore, it is possible that the mark is composed of letters and/or digits and/or a bar code for storing and representing implant-specific data. Furthermore, it is possible that the at least one mark marks a full or partial area of at least one attachment element and/or a lens body of the ophthalmologic implant. A further advantageous development of the implant according to the invention is in that it has at least two marks produced by means of different dyes. By the use of different dyes, a particularly simple and fast posture and position determination of the implant in the eye is possible. The arrangement of several marks in one or more geometric patterns also facilitates the determination of the posture and position of the implant within the eye.

In further advantageous developments of the implant according to the invention, the mark is formed during the production and/or after completion of the ophthalmologic implant. Therein, it is possible that the dye forming the mark is introduced into a lens material of the ophthalmologic implant before and/or after polymerization or vulcanization thereof, and/or is applied to a surface of the ophthalmologic implant after the polymerization or vulcanization of the lens material. However, it is also possible that even after polymerization or vulcanization of the lens material of the implant, the dye is injected into the interior or the implant body for forming the mark. If the marks are applied to the surface of the ophthalmologic implant, thus, it is possible that at least those regions of the surface of the implant, on which the mark or marks is or are disposed, are covered with a protective foil or a protective coating. Such a formation of a protective foil reliably prevents a possible washout of the dye or of the mark by the aqueous humor of the eye. If the ophthalmologic implant according to the invention is made of a hydrophobic or hydrophilic acrylate material, thus, it is for example possible to form the central region of the implant usually having optics, in particular of the intraocular lens, with a transparent, i.e. an acrylate material with a high light transmission. Then, acrylate material can be molded around this region, which contains the dye forming the mark. However, it is also possible that only the attachment elements, namely the haptics of the implants, have the mark or marks. Therein, the attachment means in turn can be composed of a material having the dye and thus the mark and afterwards be attached to the lens body. Furthermore, it is possible to dispose the marks on the implant for example by an embossing or printing procedure. Further procedures, which can be applied in implants according to the invention of plastic, are for example multicolor/multi-component injection molding procedures, back injection molding and interlayer molding procedures, so-called in-mold decorating procedures or labeling procedures, a co- or multilayer extrusion, laminating and plasma procedures such as for example chemical vapor deposition (CVD).

In further advantageous developments of the implant according to the invention, the at least one mark is applied to a foil, wherein the foil can be introduced into the ophthalmologic implant or can be applied to a surface of the ophthalmologic implant. By the use of a foil, the marks can be produced relatively simple in the printing procedure. If the foil is applied to the implant, thus, it is usually effected by means of an adhesive connection.

A microscopic system for detecting the posture and position and/or for identification of an ophthalmologic implant as previously described, in particular of an intraocular lens, includes a microscope with microscope optics, at least one illumination system for illuminating and exciting at least one mark of the ophthalmologic implant disposed in an eye, at least one camera for capturing the fluorescing or absorbing mark emitting outside of the light spectrum visible to the human, and at least one evaluation unit for at least one image of the mark captured by the camera. The microscopic system allows reliable and visible detection of the posture and position and/or identification of the ophthalmologic implant. Therein, the illumination system includes at least one light source, wherein the light source radiates white light or excitation light for the dye of the mark in a predetermined wavelength range. Therein, the type of illumination complies with the type of the used dye, the dyes suitable for the mark were already previously described in detail. The image data captured by the camera are evaluated in the evaluation unit for posture and position determination and/or identification of the implant. Therein, the evaluation unit can have at least one coupling system for coupling the captured images of the mark into the microscope optics of the microscope. Thereby, it is possible that the image data captured by the camera are superimposed on the images of the object range, i.e. the ophthalmologic implant and the structures surrounding it, for viewing by a user of the microscopic system. This also serves for exact posture and position control of the implant. Furthermore, it is possible that the evaluation unit includes at least one identification system for identification of information and identification data of the ophthalmologic implant conveyed by the mark. Therein, the thus determined data can in turn be optically blended in the microscope optics of the microscope through the coupling system, such that it can be viewed by the user. Furthermore, it is possible to forward the determined information and identification data for example to a separate display device such as a screen or even a printer. In a further advantageous development of the microscopic system, the evaluation unit includes at least one automatic tracking system for recognizing movements and/or posture and position changes of the mark and of the ophthalmologic implant. In addition, the evaluation unit can include at least one autofocus system, wherein focusing of the microscope optics to the ophthalmologic implant is effected by means of the images of the mark captured by the camera and the evaluation thereof.

In a further advantageous development of the microscopic system, the illumination system is formed as a gap illumination system. Such a gap illumination system allows that the position of the ophthalmologic implant can be better controlled after the surgical procedure. Thus, in control, the pupil does not have to be artificially expanded for example using suitable eye drops, which in turn results in the attachment elements of the implant being not visible in any event.

An optical verification method for detecting the posture and position and/or the identification of an ophthalmologic implant as previously described, in particular of an intraocular lens, includes the following steps: a) illuminating the ophthalmologic implant with at least one light source of an illumination system, wherein the light source radiates white light or excitation light for a dye of the mark of the implant in a predetermined wavelength range; b) capturing the fluorescing or absorbing mark emitting outside of the light spectrum visible to the human by means of a camera; c) evaluating at least one image of the mark captured by the camera by means of at least one evaluation unit. By the verification method, a reliable and secure detection of the posture and position and/or identification of the ophthalmologic implant are ensured. In addition, it is ensured that the application of the method does not cause any impairment of the visual sensation of view of an implant wearer, since the mark irradiated by white light or excitation light in a predetermined wavelength range emits or absorbs outside of the light spectrum visible to the human. In further advantageous developments of the verification method, the evaluation according to method step c) includes coupling the captured image of the mark into microscope optics of a microscope. Thereby, it is possible to provide a superposition image consisting of the image of the mark captured by the camera and the image of an object range, namely the observed implant and the surrounding thereof, to an observer. However, it is also possible that the evaluation according to method step c) includes identification of identification data of the ophthalmologic implant conveyed by the mark and/or the representation of information data with respect to the implant such as for example the correct positioning thereof within the eye. Therein, the identification data can include optical data or also data with respect to the material of the implant or the manufacture thereof. Furthermore, it is possible that the evaluation according to method step c) includes recognition of movements and/or posture and position changes of the mark and of the ophthalmologic implant. Furthermore, the evaluation according to method step c) can include focusing of microscope optics to the ophthalmologic implant by means of the images of the mark captured by the camera. Thereby, for example, optimum image result in capturing the marks by the camera is achieved.

BRIEF DESCRIPTION OF THE DRAWINGS

Embodiments of the invention are explained in more detail below based on schematic drawings. There show.

PREFERRED IMPLEMENTATION OF THE INVENTION

In the figures, identical or functionally identical elements are provided with the same reference characters.

Figure 1:
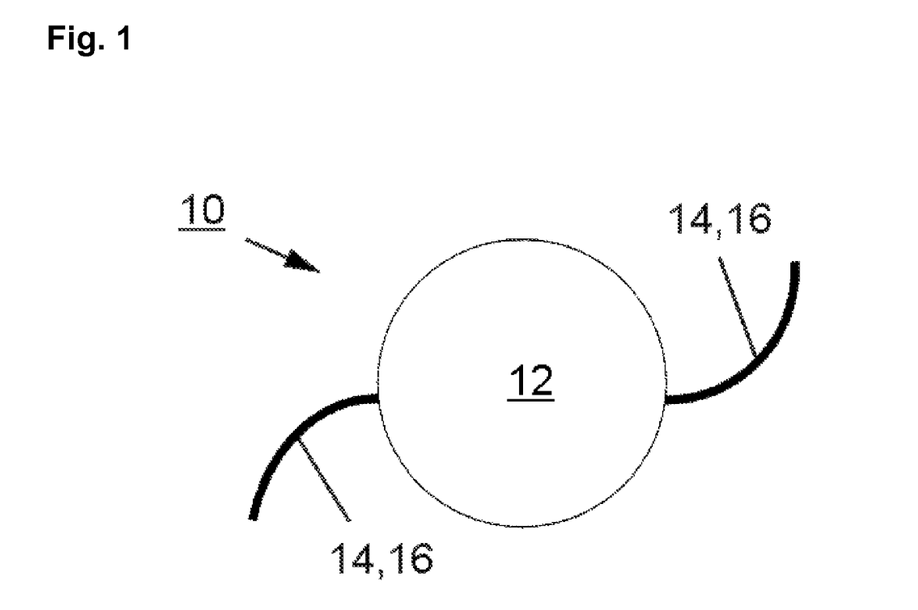
FIG. 1 a schematic representation of an ophthalmologic implant according to the invention according to a first embodiment.

In a schematic representation, in FIG. 1, a first embodiment of an ophthalmologic implant, namely of an intraocular lens 10 according to a first embodiment is illustrated. The intraocular lens 10 is composed of a lens body 12, which is formed as an optical means or has a corresponding optical means (not illustrated). At an edge 20 of the lens body 12, attachment elements 14, so-called haptics, are formed. Usually, the lens body 12 as well as the attachment elements 14 are composed of a hydrophobic or hydrophilic acrylate material. In particular, the lens body 12 and the attachment elements 14 are made of polymethyl methacrylate (PMMA) or soft copolymers consisting of a hydrophilic monomer and an alkoxyalkyl methacrylate monomer. Therein, the lens body 12 is formed such that the used material does not substantially influence the light transmission of the implant or of the intraocular lens 10 in the visual spectral range between ca. 380 nm and ca. 780 nm. Such a configuration of the implant or of the intraocular lens 10 is also used in the embodiments represented in FIGS. 2 to 9. However, it is also possible that the used material does not substantially influence the light transmission of the implant or of the intraocular lens 10 only in a partial range of the visual spectral range between ca. 450 nm and ca. 750 nm. Thus, the implant or the intraocular lens 10 can have a slight yellowness, which serves as UV protection, wherein the absorption edges of the UV protection are between ca. 400 nm and 450 nm.

Furthermore, one recognizes that in the represented first embodiment, marks 16 are formed on the respective attachment element 14. Therein, the marks 16 are each disposed in full area on the corresponding attachment element 14. Therein, the marks 16 are each made of a florescent dye with an emission maximum outside of the light spectrum visible to the human of usually 380 nm to 780 nm. However, it is also possible that an absorbing dye with an absorption maximum outside of the light spectrum visible to the human is used for producing the mark 16. In the embodiments of the intraocular lens 10 represented in FIG. 1 as well as in FIGS. 2 to 9, the fluorescent dye indocyanine green is used, the excitation wavelength of which is between 700 nm and 800 nm and the fluorescence wavelengths of which are between 805 nm and 950 nm with an emission maximum at 835 nm. To date, indocyanine green is used for microscopic examination of tissue enriched with this dye. Therein, tissue regions can be identified, in which this fluorescent dye is accumulated. Advantageously, indocyanine green has an only very low toxicity, since it is eliminated in the human body via the liver and bile ducts and is not resorbed by the intestinal mucosa.

Besides the full-area formation of the mark 16 on the attachment element 14 illustrated in FIG. 1, it is also possible to form the mark 16 in a partial area on the attachment element 14 (not illustrated). Thereby, the posture of the attachment element 14 during the positioning of the implant 10 in the eye can be clearly recognized.

Figure 2:
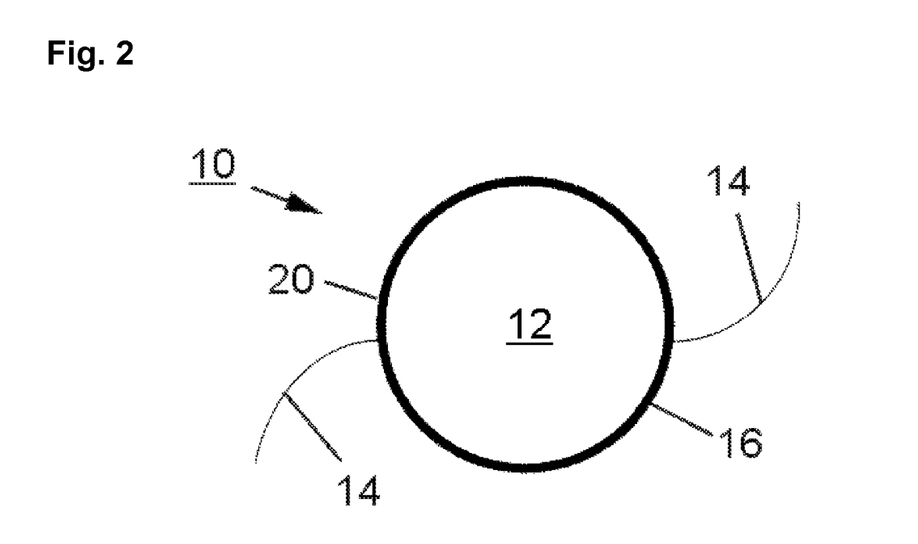
FIG. 2 a schematic representation of an ophthalmologic implant according to the invention according to a second embodiment.

FIG. 2 shows a schematic representation of an ophthalmologic implant 10, namely of an intraocular lens 10, according to a second embodiment. One recognizes that an edge region 20 of the lens body 12 is provided with an annular mark 16. The intraocular lens 10 again has two attachment elements 14, however, which are provided without marks in this embodiment.

Figure 3:
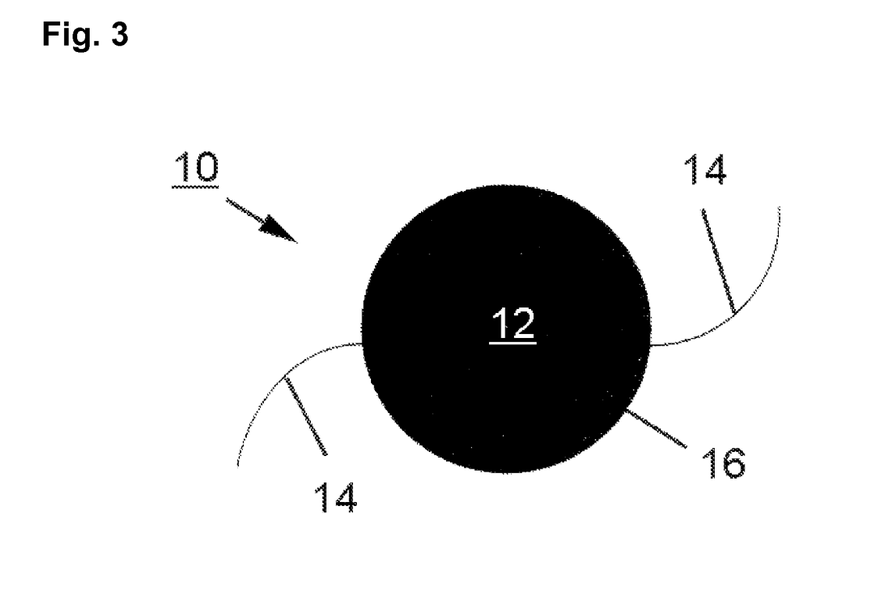
FIG. 3 a schematic representation of an ophthalmologic implant according to the invention according to a third embodiment.

FIG. 3 shows a schematic representation of an ophthalmologic implant 10, namely of an intraocular lens 10, according to a third embodiment. In this embodiment, the lens body 12 is provided with a mark 16 on the full area. However, it is also possible to form the lens body 12 only in a partial area with a mark 16 (not illustrated). A partial area configuration thus provides a further position and posture indication.

Figure 4:
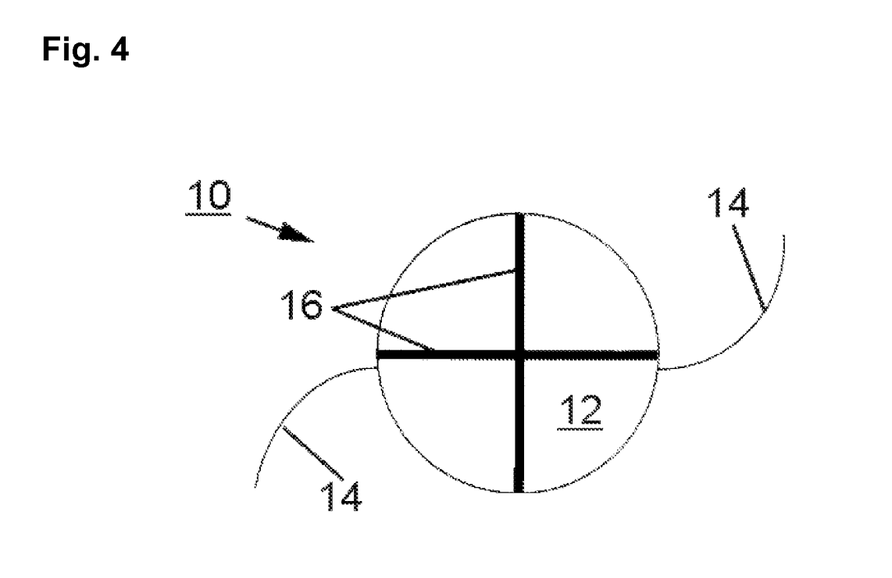
FIG. 4 a schematic representation of an ophthalmologic implant according to the invention according to a fourth embodiment.

FIG. 4 shows a schematic representation of an ophthalmologic implant 10, namely of an intraocular lens 10, according to a fourth embodiment. One recognizes that the lens body 12 has a cross-shaped mark 16. A mark 16 formed in such manner is particularly advantageous if autofocusing, movement tracking or generally the representation of the orientation of asymmetrically formed intraocular lenses is to be represented and carried out by means of appropriate devices.

Figure 5:
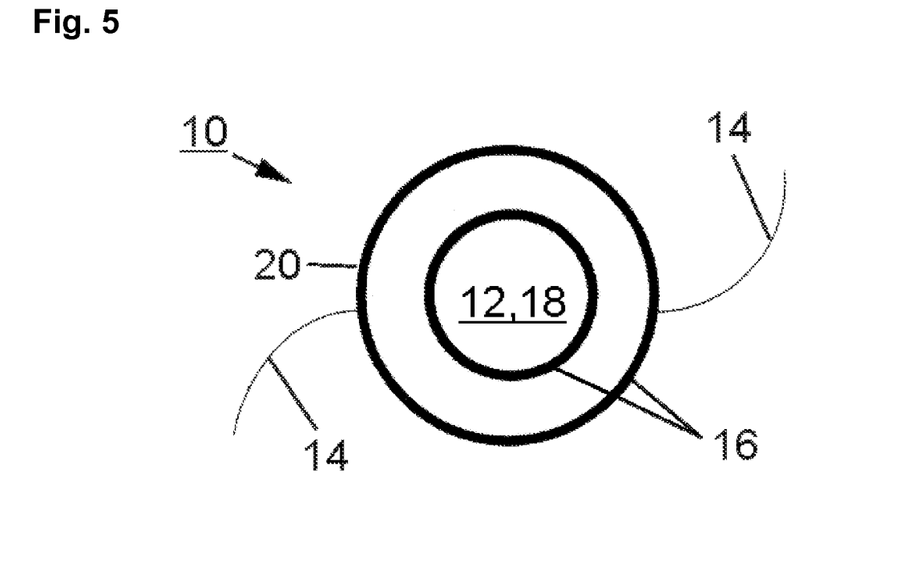
FIG. 5 a schematic representation of an ophthalmologic implant according to the invention according to a fifth embodiment.

FIG. 5 shows a schematic representation of an ophthalmologic implant 10, namely of an intraocular lens 10, according to a fifth embodiment. One recognizes that two concentric, annular marks 16 are formed on the lens body 12. Therein, an outer mark 16 surrounds the edge region 20 of the lens body 12, the inner mark 16 surrounds a central region 18 of the lens body 12. This configuration of the marks 16 too, is very well suitable for autofocus systems or tracking systems, which allow exact determination of a possible movement or also of the position and posture of the intraocular lens 10. Again, two attachment elements 14 are disposed on the lens body 12.

Figure 6:
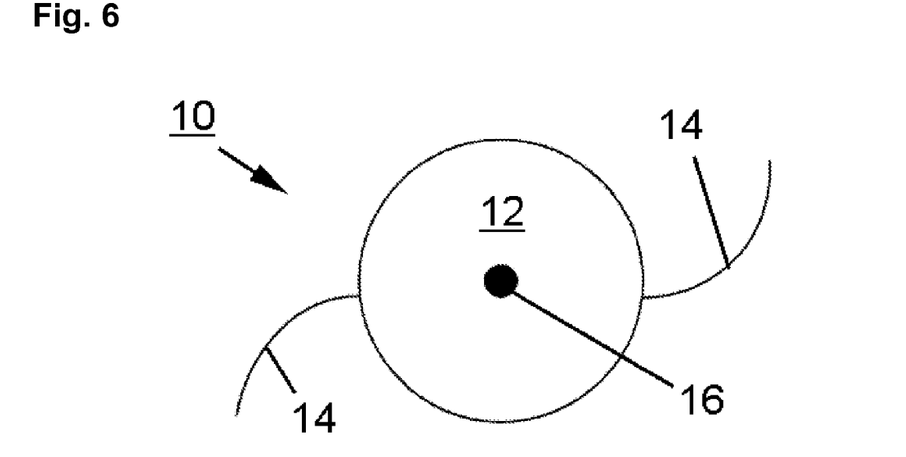
FIG. 6 a schematic representation of an ophthalmologic implant according to the invention according to a sixth embodiment.

FIG. 6 shows a schematic representation of an ophthalmologic implant 10, namely of an intraocular lens 10, according to a sixth embodiment. One recognizes that a dot-shaped mark 16 is formed in the center of the lens body 12. Furthermore, two attachment elements 14 are again formed on the lens body 12.

Figure 7:
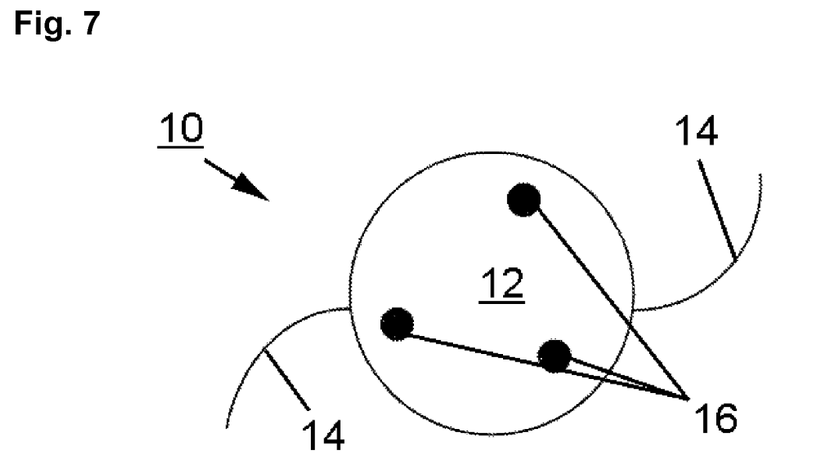
FIG. 7 a schematic representation of an ophthalmologic implant according to the invention according to a seventh embodiment.

FIG. 7 shows a schematic representation of an ophthalmologic implant 10, namely of an intraocular lens 10, according to a seventh embodiment. One recognizes that the intraocular lens 10 has plural, namely three marks 16, wherein the marks 16 are disposed in a geometric pattern. Again, two attachment elements 14 are formed on the lens body 12. The geometric arrangement of plural marks 16 is also very well suited for the use of autofocus systems or tracking systems.

Figure 8:
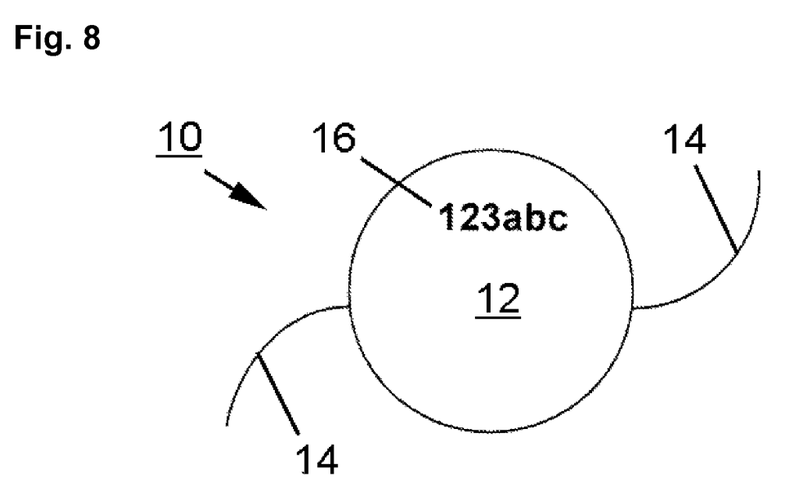
FIG. 8 a schematic representation of an ophthalmologic implant according to the invention according to an eighth embodiment.

FIG. 8 shows a schematic representation of an ophthalmologic implant 10, namely of an intraocular lens 10, according to an eight embodiment. One recognizes that the mark 16 is composed of an alphanumeric sequence consisting of letters and digits. Such marks 16 serve for identification of the intraocular lens 10, wherein in particular information with respect to the optical properties of the intraocular lens 10, the date of manufacture thereof or the material compositions thereof can be specified. Furthermore, information data with respect to the implant such as for example the correct positioning thereof within the eye can be represented. Therein, the information data is in particular superposed to the real image bound to object, independently of possible movements of the object or of the implant 10 ("augmented reality"). One recognizes that two attachments elements 14 are again formed on the lens body 12.

Figure 9:
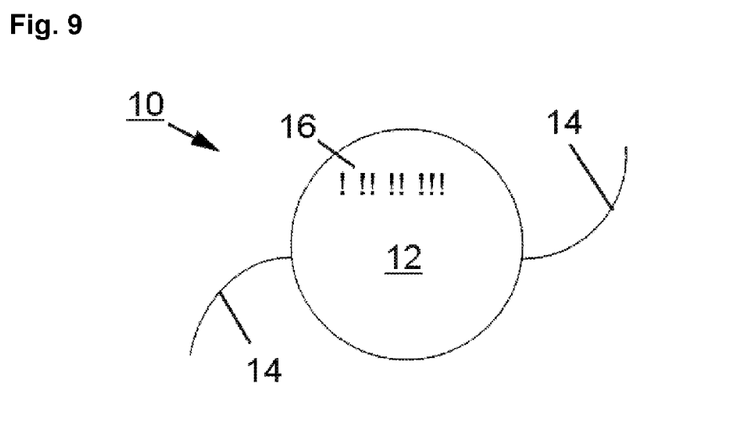
FIG. 9 a schematic representation of an ophthalmologic implant according to the invention according to a ninth embodiment.

FIG. 9 shows a schematic representation of an ophthalmologic implant 10, namely of an intraocular lens 10, with a mark 16, wherein the mark 16 is composed of a so-called bar code, which in turn can include information with respect to the intraocular lens 10. The bar code is read out by means of suitable scanning devices such that the information described in the mark 16 can be provided. Therein, the information can for example be passed to a display device or a printer and be output there.

Besides the embodiments described in FIGS. 1 to 9, a plurality of further embodiments of the ophthalmologic implant 10 or of the intraocular lens 10 are conceivable. In particular, this relates to the configuration of the marks 16, which can take each geometric shape. Furthermore, it is possible that the ophthalmologic implant 10 has at least two marks 16 produced by means of different dyes. Furthermore, the dye used for production of the mark 16 is to be biocompatible, in particular non-toxic. Finally, in all of the illustrated as well as further embodiments of the ophthalmologic implant 10, the mark 16 can be formed during production and/or after completion the ophthalmologic implant 10. Therein, for example, the dye forming the mark 16 can be introduced into the lens material of the implant 10 before and/or after polymerization or vulcanization of it. However, it is also possible that only after the polymerization or vulcanization of the lens material, the dye is applied to a surface of the ophthalmologic implant 10 or introduced in it. For this, very different procedures are available. In implants 10 of plastic, multicolor/multi-component injection molding procedures, back injection molding/interlayer molding procedures, so-called in-mold decorating procedures or labeling procedures, a co- or multilayer extrusion, laminating, printing, embossing and plasma procedures such as for example chemical vapor deposition (CVD) are to be mentioned as exemplary. However, it is also possible that the mark 16 is applied to a foil and the foil is introduced into the ophthalmologic implant 10 or is applied to a surface of the ophthalmologic implant 10. Furthermore, it is possible that marks 16 disposed on the surface of the implant 10 are coated with a protective foil or a protective coating. The protective foil and the coating in particular serve for preventing washout by for example the aqueous humor of the eye.

Figure 10:
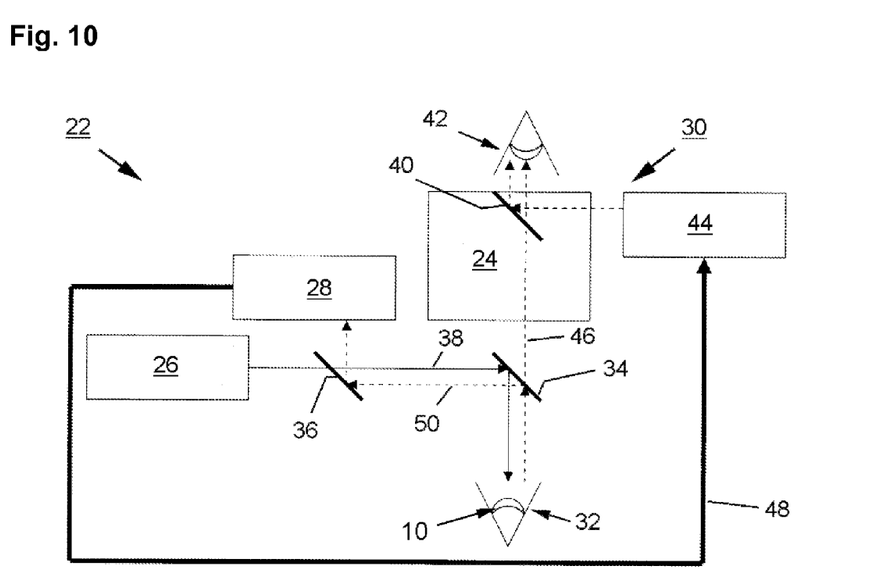
FIG. 10 a schematic representation of a microscopic system.

FIG. 10 shows a schematic representation of a microscopic system 22 for detecting the posture and position and/or for identification of an ophthalmologic implant 10, in particular of an intraocular lens 10, as it has been described in the embodiments according to FIGS. 1 to 9. Therein, the microscopic system 22 includes a microscope 24 with microscope optics, an illumination system 26 for illumination of the mark 16 composed of one or more dyes of the implant 10 disposed in an object of inspection, in particular an eye 32. Furthermore, the microscopic system 22 has a camera 28 for capturing the fluorescing or absorbing marks 16 emitting outside of the light spectrum visible to the human and at least one evaluation unit 44 for at least one image of the mark or the marks 16 captured by the camera 28. In the illustrated embodiment, the marks 16 again are composed of a dye fluorescing in the near infrared range, namely the dye indocyanine green. From FIG. 10, it becomes clear that the illumination system 26 radiates light of a certain wavelength and also white light via a beam splitter 34 to the eye 32 with the intraocular lens 10. The radiation emitted by the intraocular lens 10 or the marks 16 is sent to the camera 28, again via the beam splitter 34 and a second beam splitter 36 via a partial optical path 50. The image captured from the eye 32 or the intraocular lens 10 is provided via a further partial optical path 46 to the eye 42 of an observer via the microscope 24 with the microscope optics. For this, the beam splitter 34 is formed as a partially transparent mirror. The images captured by the camera 28 are transmitted as image data through a data line 48 to the evaluation unit 44. The evaluation unit 44 has a coupling system 30 for coupling the captured images of the mark 16 into the microscope optics of the microscope 24. Therein, the coupling system 30 includes a beam splitter or deflection mirror 40 formed as a partially transparent mirror and sending the image captured by the camera 28 and evaluated by the evaluation unit 44 to the eye 42 of the observer. Thereby, it is possible to provide a superposition image consisting of the image of the mark 16 captured by the camera 28 and the image of the object range, namely the observed implant 10 and the surrounding thereof, to an observer. Furthermore, the evaluation unit 44 can have an automatic tracking system for recognizing movements and/or posture and position changes of the mark 16 and of the implant 10. Furthermore, it is possible that the evaluation unit includes an autofocus system, wherein the focusing of the microscope optics to the implant 10 is effected by means of the images of the mark 16 captured by the camera 28 and the evaluation thereof.

The illumination system 26 includes a light source, wherein the light source radiates white light or an excitation light for the dye of the mark 16 in a predetermined wavelength range. For example, halogen lamps or laser light sources can be used as light sources. Furthermore, it is possible that the illumination system 26 is formed as a gap illumination system (not illustrated).

The microscopic system 22 as well as the intraocular lenses 10 described in the embodiments according to FIGS. 1 to 9 can be used in surgical procedures having the task of replacing a natural lens of an eye with an implant, namely an intraocular lens 10. In particular, already during insertion of the intraocular lens 10 into the corresponding region of the eye, in particular the posterior or anterior chamber of the eye, a posture and position control of the intraocular lens 10 can be effected. Thereby, secure and exact positioning of the intraocular lens in the eye is ensured.

The invention claimed is:

1. An ophthalmologic implant including at least one mark comprising a fluorescent dye with an emission maximum outside of the light spectrum visible to a human,
   wherein the fluorescent dye does not substantially influence light transmission of the implant in the visual spectral range and is from at least one structural class selected from the group consisting of cyanines, merocyanines, phthalocyanines, rhodamines, porphyrines, chlorophylls, triarylmethanes, xanthenes, oxazines, thiazines, safranines, heterocyclic pyrylium and thiapyrylium salts, perrylenes, terrylenes, quaterrylenes, quaterneles, azo dyes, metal complexes, and chinones, and
   the at least one mark designating posture or position of the implant when illuminated with white light or with light of a spectral range that effects corresponding fluorescence of the dye outside of the light spectrum visible to the human.

2. The ophthalmologic implant according to claim 1, wherein the at least one mark is formed on at least one substrate selected from the group consisting of an attachment element, a lens body, an edge of the lens body of the ophthalmologic implant and combinations thereof.

3. The ophthalmologic implant according to claim 2, wherein the at least one mark is formed during at least one step selected from the group consisting of production of the ophthalmologic implant, and after completion of the ophthalmologic implant, and wherein the mark is applied to a foil, and the foil is introduced into the ophthalmologic implant or applied to a surface of the ophthalmologic implant.

4. The ophthalmologic implant according to claim 3, wherein at least a region of the surface of the implant, on which the at least one mark is disposed, is covered with a protective foil or a protective coating.

5. The ophthalmologic implant according to claim 1, wherein the at least one mark is selected from the group consisting of letters, digits, bar code and combinations thereof.

6. The ophthalmologic implant according claim 1, wherein the at least one mark marks a full or partial area of at least one attachment element and/or a lens body of the ophthalmologic implant.

7. The ophthalmologic implant according to claim 1, wherein the ophthalmologic implant has at least two marks produced by different dyes.

8. The ophthalmologic implant according to claim 5 wherein each different dye does not substantially influence light transmission of the implant in the visual spectral range and is from one or more structural class selected from the group consisting of cyanines, merocyanines, phthalocyanines, rhodamines, porphyrines, chlorophylls, triarylmethanes, xanthenes, oxazines, thiazines, safranines, heterocyclic pyrylium and thiapyrylium salts, perrylenes, terrylenes, quaterrylenes, quaterneles, azo dyes, metal complexes, and chinones.

9. The ophthalmologic implant according to claim 8, wherein the implant does not comprise a mark comprising a dye having an emission maximum within the light spectrum visible to a human.

10. The ophthalmologic implant according to claim 1, wherein the at least one mark comprises a plurality of marks and wherein the plurality of marks are disposed in one or more geometric patterns.

11. The ophthalmologic implant according to claim 1, wherein the at least one mark is formed during at least one step selected from the group consisting of production of the ophthalmologic implant and after completion of the ophthalmologic implant, and wherein the dye forming the at least one mark is introduced into a lens material of the ophthalmologic implant during at least one dye introduction step selected from the group consisting of before polymerization of the lens material, before vulcanization of a polymeric material, after polymerization of the lens material, after vulcanization of the polymeric material, and dye application to the surface of the ophthalmologic implant after polymerization or vulcanization of the lens material.

12. The ophthalmologic implant according to claim 11, wherein at least a region of the surface of the implant, on which the at least one mark is disposed, is covered with a protective foil or a protective coating.

13. The ophthalmologic implant according to claim 11, wherein the at least one mark is formed on the implant by an embossing or printing procedure.

14. The ophthalmologic implant according to claim 1, wherein the implant is an intraocular lens.

15. An ophthalmologic implant including at least one mark composed of one or more dyes a fluorescent dye with an emission maximum outside of the light spectrum visible to a human,
   wherein the fluorescent dye does not substantially influence light transmission of the implant in the visual spectral range and is from at least one structural class selected from the group consisting of cyanines, merocyanines, phthalocyanines, rhodamines, porphyrines, chlorophylls, triarylmethanes, xanthenes, oxazines, thiazines, safranines, heterocyclic pyrylium and thiapyrylium salts, perrylenes, terrylenes, quaterrylenes, quaterneles, azo dyes, metal complexes, and chinones, and
   the at least one mark designating posture or position of the implant when illuminated with white light or with light of a spectral range that effects corresponding fluorescence of the dye outside of the light spectrum visible to the human.

16. The ophthalmologic implant according to claim 15, wherein the at least one mark is formed on at least one substrate selected from the group consisting of an attachment element, a lens body, an edge of the lens body of the ophthalmologic implant and combinations thereof.

17. The ophthalmologic implant according to claim 15, wherein the at least one mark is selected from the group consisting of letters, digits, bar code and combinations thereof.

* * * * *